United States Patent [19]

Chen

[11] 4,173,603

[45] Nov. 6, 1979

[54] METHOD FOR THE MANUFACTURE OF DIALKYL DITHIOPHOSPHORIC ACID AND DIALKYL PHOSPHOROCHLORIDOTHIONATE

[75] Inventor: Joseph L. P. Chen, Mission Viejo, Calif.

[73] Assignee: Hooker Chemicals & Plastics Corp., Niagara Falls, N.Y.

[21] Appl. No.: 865,565

[22] Filed: Dec. 29, 1977

[51] Int. Cl.$^2$ ............................ C07F 9/20; C07F 9/165
[52] U.S. Cl. ..................................... 260/986; 260/981
[58] Field of Search ................................ 260/981, 986

[56] References Cited

U.S. PATENT DOCUMENTS

| | | | |
|---|---|---|---|
| 2,862,947 | 12/1958 | Goldsmith | 260/981 OR |
| 3,515,712 | 6/1970 | Goldsmith | 260/981 X |
| 4,078,023 | 3/1978 | Lippsmeier et al. | 260/986 OR |

Primary Examiner—Anton H. Sutto
Attorney, Agent, or Firm—Peter F. Casella; William G. Gosz

[57] ABSTRACT

A continuous process for the manufacture of dialkyl dithiophosphoric acid from phosphorus pentasulfide and a lower alkanol through the use of a settling tube and a continuous process for the manufacture of dialkyl phosphorochloridothionate by chlorinating dialkyl dithiophosphoric acid with chlorine which has been diluted with an inert gas.

15 Claims, 2 Drawing Figures

METHOD FOR THE MANUFACTURE OF DIALKYL DITHIOPHOSPHORIC ACID AND DIALKYL PHOSPHOROCHLORIDOTHIONATE

BACKGROUND OF THE INVENTION

(A) Field of the Invention

This invention concerns a process for the manufacture of dialkyl phosphorochloridothionate by the chlorination of dialkyl dithiophosphoric acid. The invention further concerns a process for the preparation of dialkyl dithiophosphoric acid by reacting a lower alkyl alcohol with phosphorus pentasulfide.

(B) History of the Prior Art

Dialkyl dithiophosphoric acid (alternatively referred to as O,O-dimethyl-S-hydrogen phosphorodithioate) in the prior art was almost always manufactured in a batch process wherein a lower alkyl alcohol is reacted with solid phosphorus pentasulfide which is frequently slurried into the alcohol in a tank reactor.

Similarly, dialkyl phosphorochloridothionate (alternatively referred to as O,O-dimethyl phosphorochloridothionate) has traditionally been manufactured by chlorination of dialkyl dithiophosphoric acid in a batch process. Such batch processes, have disadvantages of high operation and labor costs and frequently a lower yield. There is now a need for large quantities of dialkyl phosphorochloridothionates for use as intermediates for insecticides such as parathion and as intermediates and for use in other known applications.

Prior art attempts to manufacture dialkyl dithiophosphoric acid and dialkyl phosphorochloridothionate in a continuous operation have had serious disadvantages.

British Pat. No. 745,858 discloses a continuous process for the manufacture of dialkyl dithiophosphates by reacting a slurry of a phosphorus sulfide with an alcohol. The process requires that a portion of the slurry be removed from the reaction vessel followed by separation of dithiophosphate product from the removed slurry. The slurry is then recycled to the reaction vessel. The process requires that slurried materials be removed, transported and maintained in a slurry form which requires expensive equipment and complicates processing.

U.S. Pat. No. 3,897,523 discloses a continuous process for the manufacture of dialkyl phosphorochloridothionates by means of a two step chlorination process. U.S. Pat. No. 3,897,523 discloses that a single stage chlorination uses an excess of chlorine to obtain a reasonable and good yield which lessens overall chlorine efficiency and promotes undesirable side reactions which reduces the product yield. U.S. Pat. No. 3,897,523 also indicates that it is necessary in a one-stage chlorination operation that the single chlorine feed be metered with a high degree of accuracy to properly control the reaction to avoid the yield losses associated with under and over chlorination.

To avoid the disadvantages which were felt to be present in a single stage chlorination operation, U.S. Pat. No. 3,897,523 discloses and claims a continuous process of producing dialkyl phosphorochloridothionates by means of a two-stage chlorination process. The process disclosed in U.S. Pat. No. 3,897,523, while resulting in increased product yield, continued to have substantial disadvantages since the process requires multiple stage reactors which in turn require independent monitoring and control equipment.

BRIEF DESCRIPTION OF THE INVENTION

In accordance with the invention, there is provided a continuous process for manufacturing both dialkyl dithiophosphoric acid and dialkyl phosphorochloridothionate which overcomes the prior art disadvantages encountered in the manufacture of these products. The manufacture of dialkyl phosphorochloridothionate is accomplished by a single step chlorination of dialkyl dithiophosphoric acid by contacting dialkyl dithiophosphoric acid with chlorine which has been diluted with a gas essentially inert to the reaction. Such inert gases include air, nitrogen or the inert gases of the periodic table of elements. The dilution of the chlorine with a gas permits the reaction to be easily controlled and results in yields as high as 90%.

The continuous process for manufacturing dialkyl dithiophosphoric acid comprises reacting a liquid lower alkyl alcohol with solid phosphorus pentasulfide slurried in dialkyl dithiophosphoric acid in a stirred tank reactor. Dialkyl dithiophosphoric acid product is separated from a major portion of slurried phosphorus pentasulfide by means of a settling tube partially immersed in the slurry within the reactor and removing the separated dialkyl dithiophosphoric acid from the top portion of the settling tube at a fluid velocity at least as slow as the settling velocity of a major portion of the slurried phosphorus pentasulfide.

DETAILED DESCRIPTION OF THE INVENTION

Figure 1:
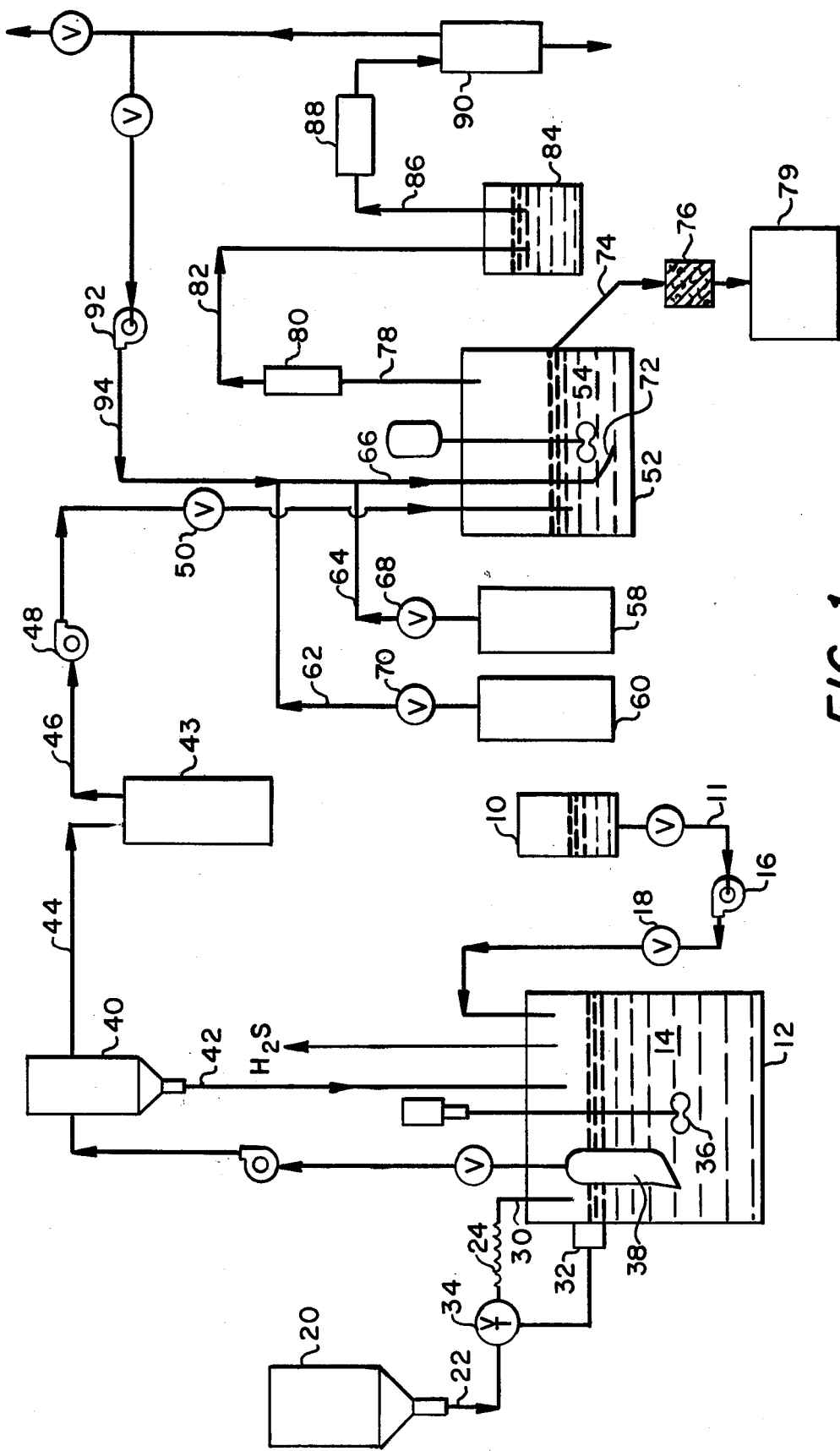
FIG. 1 is a schematic diagram of the process of the invention.

In accordance with the invention, there is provided a continuous process for manufacturing dialkyl dithiophosphoric acid by reacting a liquid lower alkyl alcohol such as methanol or ethanol with solid phosphorus pentasulfide and for preparing dialkyl phosphorochloridothionate by chlorination of dialkyl dithiophosphoric acid.

While not wishing to be bound by any particular reaction sequence, the stoichiometric equations for the manufacture of dialkyl dithiophosphoric acid and dialkyl phosphorochloridothionate are believed to be as follows:

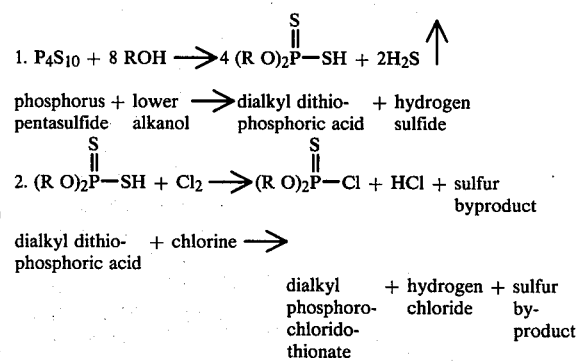

wherein R is a lower alkyl radical of 1 to 4 carbon atoms which is preferably a methyl or ethyl group.

In preparing dialkyl phosphorochloridothionate from dialkyl dithiophosphoric acid, a slight excess, i.e. from about 5 to about 25 weight percent and preferably about 10 to about 20 weight percent excess, of chlorine is desirably used. The slight excess of chlorine has been unexpectedly found to substantially increase the yield of dialkyl phosphorochloridothionate. Some chlorine is believed to combine with sulfur to form a reaction by product primarily comprising a complex sulfur chloride.

The improvement for the continuous process for manufacturing dialkyl dithiophosphoric acid in accordance with the invention comprises separating dialkyl dithiophosphoric acid product from a major portion of slurried phosphorus pentasulfide by means of a settling tube partially immersed in the slurry within a reactor and removing the separated dialkyl dithiophosphoric acid product from a top portion of the settling tube at a fluid velocity at least as slow as the settling velocity of a major portion of the slurried phosphorus pentasulfide. In manufacturing the dialkyl dithiophosphoric acid, a heel of dialkyl dithiophosphoric acid product is introduced into a tank reactor and phosphorus pentasulfide ($P_4S_{10}$) is introduced at a volume ratio of from about 1:5 to about 1:1 and preferably about 1:3 phosphorus pentasulfide to dialkyl dithiophosphoric acid. Methanol is continuously fed into the reactor. A screw feeder or another suitable solid feeding device, activated by a solid concentration or density indicator of the slurry, is used to feed solid $P_4S_{10}$ continuously or intermittently into the reactor to maintain the proper concentration of $P_4S_{10}$. Slurry within the reactor is adequately agitated to ensure intimate contact of solid reactant $P_4S_{10}$ with alchohol. Hydrogen sulfide by-product evolves from the reaction and may be disposed of by absorbing the gas chemically or reducing it to elemental sulfur by means of a Clause process. The liquid product is separated from the slurry by employing a settling tube partially immersed in the slurry to settle out a major portion of the solid particles of $P_4S_{10}$.

"Major portion" as used herein means at least about 90 percent of solid $P_4S_{10}$ is removed by means of the settling tube.

The product from the top of the settling tube is preferably pumped or siphoned to an apparatus for further removal of residual phosphorus pentasulfide. The apparatus for removal of residual phosphorus pentasulfide may be any solid separating apparatus such as a filter or centrifuge. In the preferred embodiment of the invention, a hydroclone is utilized for removal of residual $P_4S_{10}$ which is returned to the reactor for further processing. The resulting dialkyl dithiophosphoric acid product contains from about 2 to about 6 percent unreacted alcohol which may be removed by further purification or, where the product is used as an intermediate for the preparation of dialkyl phosphorochloridothionate, may be fed directly to a chlorination reactor without purification. When the dialkyl dithiophosphoric acid is used as such an intermediate, it has been found that the presence of a small amount of lower alkyl alcohol as previously described actually seems to be beneficial since somewhat higher yields of dialkyl phosphorochloridothionate are obtained when from about 2 to about 6 percent of a lower alkanol such as methanol is present.

The settling tube 38 has a bottom opening which is preferably bent to one side to minimize hydrogen sulfide gas from entering into the tube. The bottom end of the tube is immersed in the slurry and has an inner surface which is sufficiently inclined to allow settled solid $P_4S_{10}$ to flow from the tube to the reactor. The diameter of the tube is selected in such a way that the tube is large enough to remove the liquid product at a liquid withdraw velocity equal to or smaller than the solid settling velocity of a major portion of the $P_4S_{10}$. Control of the liquid withdrawal rate can be done manually or by a pump activated by a liquid (or slurry) level indicator in the reactor.

The process for preparation of dialkyl dithiophosphoric acid is generally carried out at a temperature between about 20° and about 65° C. and may be as high as about 125° C. Temperatures between about 75° and 125° C. are, however, generally not preferred since the risk of an uncontrolled reaction increases with the temperature. At a temperature of 125° C. or above, the heat of reaction becomes difficult to manage. The reaction temperature is somewhat dependent upon the reactivity of the $P_4S_{10}$ used in the process and the residence time required for a moderately reactive $P_4S_{10}$, e.g. distilled ground powder, is from about 2 to about 20 hours. The feed ratio of alcohol to $P_4S_{10}$ is desirably about stoichiometric. A slight excess of alcohol, such as about 3 to about 15 weight percent has been found to result in improved yield and is thus preferred. The reactor is preferably always filled with excess $P_4S_{10}$, i.e. volume ratio of solid $P_4S_{10}$ to liquid dialkyl dithiophosphoric acid of 0.2:1 or greater. The reaction should be carried to substantial completion so that only a small amount, i.e. from about 2 to about 6 weight percent of alcohol remains in the product. The overall process efficiency can be as high as 97 percent.

An organophosphorus by product in an amount of from about 2 to about 6 percent frequently results which is largely O,O,S-trialkyl dithiophosphate and O,O,O-trialkyl thiophosphate. The majority of organophosphorus by product is O,O,S-trialkyl dithiophosphate which will convert to dialkyl phosphorochloridothionate upon chlorination.

The continuous process for the manufacture of dialkyl phosphorochloridothionate by chlorination of dialkyl dithiophosphoric acid comprises chlorinating dialkyl dithiophosphoric acid, particularly, dimethyl dithiophosphoric acid (DMTA) or diethyl dithiophosphoric acid (DETA), in a one-stage continuous flow reactor. The process comprises feeding liquid dialkyl dithiophosphoric acid into a reactor containing dialkyl phosphorochloridothionate product as a heel and simultaneously feeding gaseous chlorine diluted with an inert gas. "Inert gas" as used herein is a gas which essentially is inert to the reaction of dialkyl dithiophosphoric acid with chlorine. Such gases include but are not limited to the inert gases of the periodic table of the elements. The inert gas may be air but is preferably nitrogen which is sparged into the bottom of the chlorination reactor. The molar ratio of dialkyl dithiophosphoric acid to chlorine is maintained between about 1:1.05 to about 1:1.20. The most preferable ratio of dialkyl dithiophosphoric acid to chlorine is about 1:1.15. The inert diluting gas, after having been cleaned in a waste gas cleaning system can be recycled. The chlorination reactor as previously mentioned, is heeled with dialkyl phosphorochloridothionate which may be initially produced in a batch operation. The dialkyl dithiophosphoric acid and diluted chlorine gas feeds are blended in the reactor with sufficient agitation to form uniform blend and to obtain a uniform temperature. Temperature control of the reactor can be done by an outside jacket or internal cooling coils. Refluxing entrained dialkyl phosphorochloridothionate to the reactor by condensation may also assist in temperature control.

The product from the chlorinator is continuously removed which controls the liquid level in the reactor and the product is filtered to remove sulfur which may precipitate. The dialkyl phosphorochloridothionate product is then stored for further reaction, shipping or purification. The product gas stream consisting of entrained product, HCl, CH$_3$Cl, and unreacted diluting gas is desirably treated by passing the gas through a condenser for returning product to the reactor. HCl and CH$_3$Cl may be removed by any known means such as scrubbing the gas with a caustic solution to remove HCl and freezing the gas to remove CH$_3$Cl. The remaining unreacted diluting gas may then be recycled to the process. The process requires only one simple stirred tank reactor and offers the advantages of simple construction and operation.

The process is generally carried out at a temperature of between about 0° C. and 65° C. and is preferably carried out between about 55 and about 65°. Temperatures above 75° C. may be used but are less desirable because the reaction is more difficult to control. At a temperature of about 125° C., the reaction rapidly becomes sufficiently exothermic so that it is difficult to control.

As previously discussed, the inert diluting gas can be air, nitrogen or an inert gas of the periodic table of elements, such as argon. The preferred inert gas is nitrogen due to its highly non-reactive character, availability and cost. Air can be used as the inert gas since air does not substantially interfere with the reaction. A very small quantity of oxygen in air does, however, react and is therefore not the preferred inert gas. The volume ratio of diluting gas to chlorine is preferably a volume ratio of from about 1:1 to about 20:1. High diluting ratios, e.g. 20:1 improve yields, however, large gas flow through the reactor can entrain too much liquid product and increase reaction time due to poor gas-liquid contact because of filling the reactor with large volumes of gas. Low diluting ratios, e.g. 1:1, may not have an entrainment problem, but the yield will be reduced by as much as 5 to 15 percent due to side reactions caused by the high localized chlorine concentrations. The most preferred diluting ratio is from about 5:1 to about 12:1.

The residence time required for chlorinating the dialkyl dithiophosphoric acid is usually from about 30 to about 120 minutes. Yields of from about 85 to about 90 percent have been obtained with a residence time of about 60 minutes when the feed ratio of the dialkyl dithiophosphoric acid to Cl$_2$ is from about 1:1.05 to about 1:1.20. The product purity can be as high as from about 70 to about 76 percent without further purification.

Referring now to the drawings, FIG. 1 is a schematic flow diagram illustrating a combined novel process for the manufacture of dialkyl phosphorochloridothionate from phosphorus pentasulfide (P$_4$S$_{10}$), lower alkyl alcohol, and chlorine with the intermediate preparation of dialkyl dithiophosphoric acid. In the process of the invention, alcohol from either the alcohol product feedline or alcohol storage tank 10 is fed through line 11 to reaction vessel 12 which contains a heel of dialkyl dithiophosphoric acid 14, by means of alcohol supply pump 16. The supply of alcohol is monitored and controlled by means of a flow meter and valve 18. Phosphorus pentasulfide from scale 20 flows through line 22 to screw feeder 24. Screw feeder 24 forces phosphorus pentasulfide through line 30 into tank 12. Continuous monitoring of solids content in tank 12 is accomplished by means of indicator 32 which opens valve 34 to permit the addition of more phosphorus pentasulfide through screw feeder 24 when required. Agitator 36 maintains a slurry of phosphorus pentasulfide in dialkyl dithiophosphoric acid and alcohol in vessel 12.

Liquid product dialkyl dithiophosphoric acid is separated from the slurry located in tank 12 by means of settling tube 38 which is partially immersed in the slurry to precipitate out most of the solid particles. In the preferred embodiment, the liquid product is pumped or siphoned up to hydroclone 40 which removes residual phosphorus pentasulfide. The phosphorus pentasulfide removed by hydroclone 40 is returned to the reactor 12 through tube 42.

Finished product from hydroclone 40 passes to storage vessel 43 through line 44. The dialkyl dithiophosphoric acid product may then be used to feed a continuous process for the manufacture of dialkyl phosphorochloridothionate or may be removed to storage for other purposes.

In preparing dialkyl phosphorochloridothionate, dialkyl dithiophosphoric acid passes from storage tank 43 through line 46 by means of pump 48 through metering valve 50 to a chlorination reactor 52 which contains a heel of dialkyl phosphorochloridothionate 54. The flow of the dialkyl dithiophosphoric acid is metered and controlled by metering valve 50. Chlorine from a chlorine storage tank 58 and diluting gas which is preferably nitrogen from a storage tank 60 pass through lines 62 and 64 respectively and blend in line 66. The flow of chlorine and diluting gas are controlled by metering valves 68 and 70 respectively. The blend of chlorine and diluting gas pass through line 66 to sparge ring 72 which is located in chlorination reactor 52. Dialkyl phosphorochloridothionate is removed from chlorination reactor 52 through line 74 and filter 76 to a storage vessel 79. The resulting dialkyl phosphorochloridothionate may be further purified by distillation and washing. Vapor and gas from reaction vessel 52 pass through line 78 to condenser 80 which removes entrained product which flows back to chlorination reactor 52.

The vapor and gas then pass from condenser 80 through line 82 to scrubber 84 which removes hydrogen chloride. Gas from scrubber 84 then passes through line 86 and dryer 88 to freezer 90 wherein CH$_3$Cl is removed. The remaining gas is essentially diluting gas which may be compressed by compressor 92 and returned through line 94 to form a part of the diluting gas for dilution of chlorine.

Figure 2:
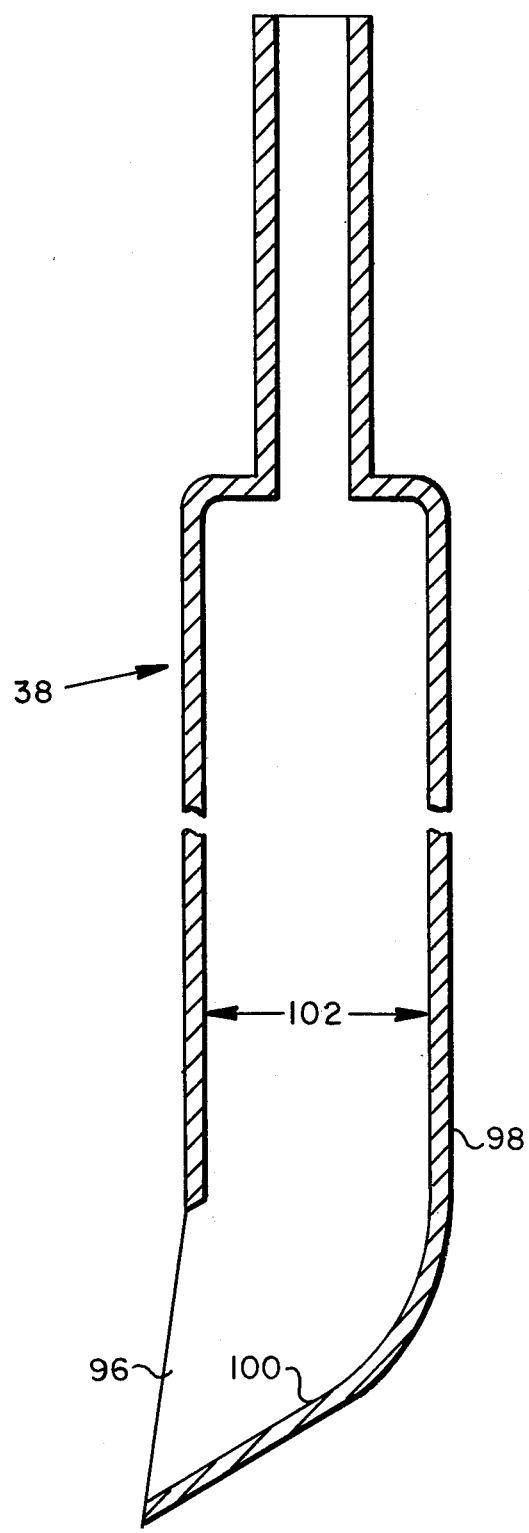
FIG. 2 is a cross sectional view of the settling tube of the preferred embodiment of the invention for the manufacture of dialkyl dithiophosphoric acid.

As best seen in FIG. 2, the settling tube 38 utilized in the process has a bottom opening 96 which is bent to one side. The bottom end 98 of tube 38 is immersed in the slurry 14 and has an inner surface 100 which is sufficiently inclined to allow settled solids to flow from tube 38 back into the reactor. The inside diameter 102 of the tube is selected in such a way that liquid product can be removed at a withdraw velocity equal to or smaller than the solid settling velocity of a major portion of the phosphorus pentasulfide.

The following examples serve to illustrate but not limit the novel continuous processes of the invention. Unless otherwise indicated, all parts and percentages are by weight.

EXAMPLE I

To a heel of 1250 ml consisting of a slurry of 417 ml of distilled ground $P_4S_{10}$ in 833 ml of dimethyl dithiophosphoric acid (i.e., DMTA) were added 1.3 ml per minute of anhydrous methanol and 1.7 grams per minute of $P_4S_{10}$. The slurry was well agitated at 55° C. and solid-free DMTA was continuously withdrawn through a 1½" diameter settling tube at a rate of 1.89 ml per minute. The product contains 94 weight percent of DMTA and 6 percent of organophosphorus by product which is largely a mixture of O,O,S-trimethyl dithiophosphate and O,O,O-trimethyl thiophosphate. The product also contains about 4 weight percent of methanol based upon the combined weight of DMTA and organophosphorus by product.

EXAMPLE II

To the same heel of Example I was added 1.417 ml per minute of anhydrous methanol and 1.935 grams per minute of $P_4S_{10}$. The reactor was maintained at 55° C. and solid-free DMTA was withdrawn at 2.20 ml per minute. The product contains 92 weight percent of DMTA and 8 percent of organophosphorus by product. The product also contains about 4 weight percent of methanol based upon combined weight of DMTA and organophosphorus by product.

EXAMPLE III

To the heel of Example I was added 1.489 ml per minute of anhydrous methanol and 2.085 grams per minute of $P_4S_{10}$. The reactor was maintained at 55° C. as solid-free DMTA was withdrawn at a rate of 2.274 ml per minute. The product contains 93 weight percent of DMTA and 7 weight percent of organophosphorus by product and 4 weight percent of methanol based upon a combined weight of DMTA and organophosphorus by product.

EXAMPLE IV

To a heel of 180 ml of dimethyl phosphorochloridothionate (DMPCT) at a purity of 65 weight percent was added 0.024 moles per minute of DMTA at a purity of 92 weight percent and 0.027 moles per minute of chlorine. The mixture was well agitated at 60° C. and 0.031 moles per minute of the product was continuously withdrawn from the reactor. The product is 55 weight percent pure and the yield is about 74 percent based upon DMTA feed.

EXAMPLE V

To a heel of 223 ml of dimethyl phosphorochloridothionate at a purity of 70 weight percent was added 0.0245 moles per minute of DMTA (purity of 92 weight percent) and 0.0271 moles per minute of $Cl_2$ diluted with 0.27 moles per minute of air. The mixture was well agitated at 60° C. and 0.0272 moles per minute of the product was continuously withdrawn from the reactor. The product is 69 weight percent pure and the yield is 80 percent based upon DMTA feed.

EXAMPLE VI

To a heel of 130 ml of DMPCT at a purity of 64 weight percent was added 0.023 moles per minute of DMTA (purity of about 92 percent) and 0.027 moles per minute of $Cl_2$ diluted with 0.27 moles per minute of $N_2$. The mixture was well agitated at 60° C. and 0.024 moles per minute of the product was continuously withdrawn from the reactor. The product is 73 weight percent pure and the yield is about 84 percent based upon DMTA feed.

EXAMPLE VII

To the same heel shown in Example VI is added 0.024 moles per minute of DMTA (purity of about 93 percent) and 0.0275 moles per minute of $Cl_2$ diluted with 0.275 moles per minute of $N_2$. The mixture was well agitated at 60° C. and 0.0256 moles per minute of the product was continuously withdrawn from the reactor. The product is 76 percent pure and the yield is about 89 percent based upon DMTA feed.

What is claimed is:

1. A continuous process for manufacturing dialkyl phosphorochloridothionate which comprises:
    (a) continuously reacting a liquid lower alkyl alcohol with solid phosphorus pentasulfide slurried in dialkyl dithiophosphoric acid;
    (b) partially immersing a settling tube having an inclined inner surface in said slurry to separate dialkyl dithiophosphoric acid product from a major portion of slurried phosphorus pentasulfide;
    (c) removing said separated dialkyl dithiophosphoric acid product from a top portion of said settling tube at a fluid velocity at least as slow as the settling velocity of a major portion of said slurried phosphorus pentasulfide;
    (d) continuously reacting said removed dialkyl dithiophosphoric acid with chlorine in a single step operation by contacting said removed dialkyl dithiophosphoric acid with chlorine at a temperature of from 0° to about 75° C., said chlorine having been diluted with an inert gas; and
    (e) separating the resulting dialkyl phosphorochloridothionate from the reaction mixture.

2. The process of claim 1 wherein the residence time of said removed dialkyl dithiophosphoric acid with chlorine is from about 30 to about 120 minutes and the ratio of inert gas to chlorine is from about 5:1 to 15:1.

3. In a continuous process for manufacturing dialkyl dithiophosphoric acid by reacting a liquid lower alkyl alcohol with solid phosphorus pentasulfide slurried in dialkyl dithiophosphoric acid in a stirred tank reactor, the improvement which comprises the steps of:
    (a) partially immersing a settling tube having an inclined inner surface in said slurry to separate dialkyl dithiophosphoric acid product from a major portion of slurried phosphorus pentasulfide; and
    (b) removing said separated dialkyl dithiophosphoric acid product from a top portion of said settling tube at a fluid velocity at least as slow as the settling velocity of a major portion of said slurried phosphorus pentasulfide.

4. The process of claim 3 wherein said lower alkyl alcohol is methanol or ethanol and said dialkyl dithiophosphoric acid is dimethyl dithiophosphoric acid or diethyl dithiophosphoric acid.

5. The process of claim 4 wherein said removed dissolved dialkyl dithiophosphoric acid is further purified by removing residual phosphorus pentasulfide.

6. The process of claim 5 wherein said residual phosphorus pentasulfide is removed in a hydroclone.

7. The process of claim 5 wherein the residence time of phosphorus pentasulfide with alcohol is from to about 2 to about 12 hours and the reaction temperature is from about 20° to about 65° C.

8. In a continuous process for the manufacture of dialkyl phosphorochloridothionate by chlorination of dialkyl dithiophosphoric acid, the improvement which comprises chlorinating dialkyl dithiophosphoric acid in a single step operation by contacting dialkyl dithiophosphoric acid with chlorine which has been diluted with an inert gas, wherein the ratio of inert gas to chlorine is from about 5:1 to about 15:1.

9. The process of claim 8 wherein said diluting gas is nitrogen.

10. The process of claim 8 wherein the dialkyl phosphorochloridothionate is dimethyl phosphorochoridothionate or diethyl phosphorochloridothionate.

11. The process of claim 10 wherein the residence time of said dialkyl dithiophosphoric acid with chlorine is from about 30 to about 120 minutes and the molar ratio of the contacted dialkyl dithiophosphoric acid to chlorine is between about 1:1.05 and 1:1.20.

12. The process of claim 10 wherein said dialkyl dithiophosphoric acid contains from about 2 to about 6 weight percent of methanol or ethanol.

13. The process of claim 8 wherein said ratio of inert gas to chlorine is from about 5:1 to about 12:1.

14. The process of claim 11 wherein said dialkyl dithiophosphoric acid is reacted with chlorine at a temperature of from 0° to about 65° C.

15. The process of claim 14 wherein the reaction temperature is from about 55° to about 65° C.

* * * * *